(12) United States Patent
Lee et al.

(10) Patent No.: US 8,961,875 B2
(45) Date of Patent: Feb. 24, 2015

(54) METHODS FOR INACTIVATING FLUID CULTURES THROUGH HEATING

(71) Applicant: Hyclone Laboratories, Inc., Logan, UT (US)

(72) Inventors: Jacob D. Lee, Smithfield, UT (US); Whitt F. Woods, North Ogden, UT (US)

(73) Assignee: Life Technologies Corporation, Carlsbad, CA (US)

(*) Notice: Subject to any disclaimer, the term of this patent is extended or adjusted under 35 U.S.C. 154(b) by 0 days.

(21) Appl. No.: 14/075,933

(22) Filed: Nov. 8, 2013

(65) Prior Publication Data
US 2014/0065015 A1    Mar. 6, 2014

Related U.S. Application Data

(62) Division of application No. 12/986,734, filed on Jan. 7, 2011, now Pat. No. 8,608,369.

(51) Int. Cl.
*A61L 2/00* (2006.01)
*B01F 7/00* (2006.01)
*B01F 7/16* (2006.01)
*B01F 15/00* (2006.01)
*B01F 15/06* (2006.01)
*F24H 1/12* (2006.01)

(52) U.S. Cl.
CPC .......... *A61L 2/0023* (2013.01); *B01F 7/00375* (2013.01); *B01F 7/00691* (2013.01); *B01F 7/00725* (2013.01); *B01F 7/1695* (2013.01); *B01F 15/00006* (2013.01); *B01F 15/0072* (2013.01); *B01F 15/00785* (2013.01); *B01F 15/0085* (2013.01); *B01F 15/063* (2013.01); *B01F 2015/062* (2013.01); *F24H 1/122* (2013.01)
USPC ............................................. 422/38; 366/145

(58) Field of Classification Search
CPC ................................ A61L 2/00; A61L 2/0023
USPC ............................................. 422/38; 366/145
See application file for complete search history.

(56) References Cited

U.S. PATENT DOCUMENTS

| | | | |
|---|---|---|---|
| 2,162,400 | A | 6/1939 | Heath |
| 2,797,903 | A | 7/1957 | Urban |
| 3,647,397 | A | 3/1972 | Coleman |
| 4,711,582 | A | 12/1987 | Kennedy |
| 4,805,799 | A | 2/1989 | Robbins, III |

(Continued)

FOREIGN PATENT DOCUMENTS

| | | |
|---|---|---|
| DE | 102 01 811 | 7/2003 |
| EP | 0 239 962 | 10/1987 |

(Continued)

*Primary Examiner* — Sean E Conley
(74) *Attorney, Agent, or Firm* — Workman Nydegger

(57) ABSTRACT

A method for inactivating a fluid culture includes inserting a collapsible bag within a chamber of a tank assembly. A fluid is dispensed into a compartment of the collapsible bag, the fluid including a culture containing live cells or microorganisms. A lid is positioned over an opening of the tank assembly so that the collapsible bag is substantially enclosed within the tank assembly. The fluid within the collapsible bag is heated to an inactivation temperature that is sufficiently high to kill all of the live cells or microorganisms within the fluid. In one embodiment, the fluid within the flexible bag is mixed while the fluid is being heated to the inactivation temperature.

16 Claims, 12 Drawing Sheets

(56) References Cited

U.S. PATENT DOCUMENTS

| | | |
|---|---|---|
| 4,828,395 A | 5/1989 | Saito et al. |
| 5,422,043 A | 6/1995 | Burris |
| 5,458,771 A | 10/1995 | Todd |
| 5,584,577 A | 12/1996 | Thies |
| 5,727,878 A | 3/1998 | Sullivan, Jr. |
| 5,799,830 A | 9/1998 | Carroll et al. |
| 5,858,283 A | 1/1999 | Burris |
| 5,941,635 A | 8/1999 | Stewart |
| 5,988,422 A | 11/1999 | Vallot |
| 6,071,005 A | 6/2000 | Ekambaram et al. |
| 6,076,457 A | 6/2000 | Vallot |
| 6,083,587 A | 7/2000 | Smith et al. |
| 6,245,555 B1 | 6/2001 | Curtis |
| 6,494,613 B2 | 12/2002 | Terentiev |
| 6,655,655 B1 | 12/2003 | Matkovich et al. |
| 6,670,171 B2 | 12/2003 | Carll |
| 6,709,862 B2 | 3/2004 | Curtis |
| 6,773,678 B2 | 8/2004 | Cummings et al. |
| 6,908,223 B2 | 6/2005 | Bibbo et al. |
| 6,981,794 B2 | 1/2006 | Bibbo et al. |
| 7,070,318 B2 | 7/2006 | Renfro |
| 7,153,021 B2 | 12/2006 | Goodwin et al. |
| 7,384,783 B2 | 6/2008 | Kunas et al. |
| 7,487,688 B2 | 2/2009 | Goodwin |
| 7,682,067 B2 | 3/2010 | West et al. |
| 7,901,934 B2 | 3/2011 | Kunas et al. |
| 2002/0105856 A1 | 8/2002 | Terentiev |
| 2002/0145940 A1 | 10/2002 | Terentiev |
| 2004/0062140 A1 | 4/2004 | Cadogan et al. |
| 2004/0136265 A1 | 7/2004 | Meier et al. |
| 2004/0190372 A1 | 9/2004 | Goodwin et al. |
| 2005/0002274 A1 | 1/2005 | Terentiev |
| 2005/0276158 A1 | 12/2005 | Thomas |
| 2006/0280028 A1 | 12/2006 | West et al. |
| 2009/0126515 A1 | 5/2009 | Goodwin |
| 2011/0188928 A1 | 8/2011 | West et al. |
| 2011/0310696 A1 | 12/2011 | Goodwin et al. |

FOREIGN PATENT DOCUMENTS

| | | |
|---|---|---|
| EP | 03143885 | 11/1989 |
| GB | 2202549 A | 9/1988 |
| JP | 60-151400 | 10/1985 |
| JP | 1-180228 | 7/1989 |
| JP | 2-035925 | 2/1990 |
| JP | 2-057174 | 2/1990 |
| JP | 5-284966 | 11/1993 |
| JP | 6-285353 | 10/1994 |
| JP | 8-108057 | 4/1996 |
| JP | 10-073164 | 3/1998 |
| JP | 11-028346 | 2/1999 |
| JP | 2001-224938 | 8/2001 |
| JP | 2005-080662 | 3/2005 |
| WO | 2005/068059 | 7/2005 |

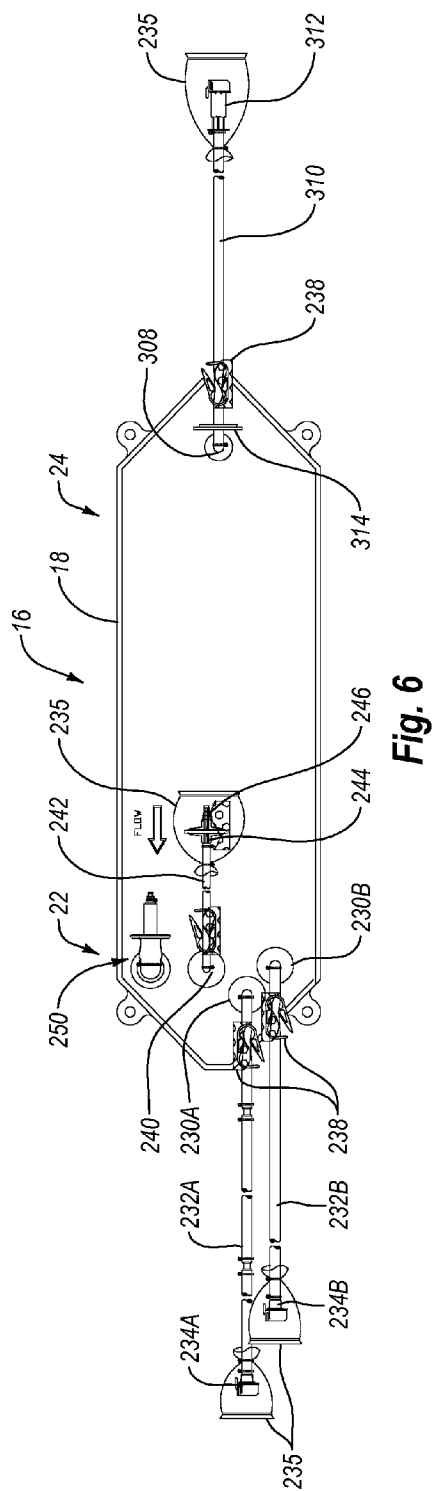
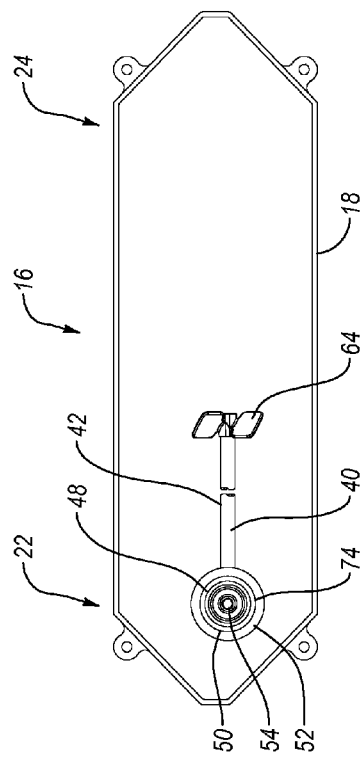

METHODS FOR INACTIVATING FLUID CULTURES THROUGH HEATING

CROSS-REFERENCE TO RELATED APPLICATIONS

This application is a divisional of U.S. application Ser. No. 12/986,734, filed Jan. 7, 2011, which is incorporated herein by specific reference in its entirety.

BACKGROUND OF THE INVENTION

1. The Field of the Invention

The present invention relates to systems and methods for heating and mixing fluids which can be used for inactivating cells or microorganisms.

2. The Relevant Technology

The biopharmaceutical industry uses a broad range of mixing systems for a variety of processes such as in the preparation of media and buffers and in the growing or processing of cells and microorganisms. Many conventional mixing systems, including bioreactors, comprise a rigid tank that can be sealed closed. A drive shaft with impeller is rotatably disposed within the tank. The impeller functions to suspend and mix the components.

In many cases, great care must be taken to sterilize and maintain the sterility of the mixing system so that the culture or other product does not become contaminated. Accordingly, between the production of different batches, the mixing tank, mixer, and all other reusable components that contact the processed material must be carefully cleaned to avoid any cross contamination. The cleaning of the structural components is labor intensive, time consuming, and costly. For example, the cleaning can require the use of chemical cleaners such as sodium hydroxide and may require steam sterilization as well. The use of chemical cleaners has the additional challenge of being relatively dangerous, and cleaning agents can be difficult and/or expensive to dispose of once used.

Once processing step commonly used with biological fluids containing a culture is to heat the fluid to a defined temperature to kill or inactivate the cells or microorganisms therein. This has historically been accomplished by heating the fluid within a stainless steel tank. Such processing, however, again requires the cleaning and sterilization of the tank between different batches.

Accordingly, what is needed in the art are system that permit controlled and uniform heating of a fluid that does not require washing or sterilization between batches and that minimizes any potential for breach in sterility.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 6 is a front side plan view of the container assembly shown in FIG. 1 in a collapsed position;

FIG. 7 is a back side plan view of a container assembly shown in FIG. 6 in a collapsed position;

DETAILED DESCRIPTION OF THE PREFERRED EMBODIMENTS

The present invention relates to systems and methods for heating fluids but can also be used for mixing and/or cooling fluids. The systems can commonly be used for inactivating cells or microorganism in a biological fluid by heating the fluid. For example, the systems can be used for inactivating yeast cells by heating media containing the cells to a defined temperature and then holding the media at the temperature for a defined time. The systems can be used with other cells or microorganism and can be used for heating and/or mixing other biological or non-biological fluids for other purposes such as sterilization or fluid processing.

The inventive systems are designed so that a majority of the system components that contact the material being processed can be disposed of after each use. As a result, the inventive systems substantially eliminate the burden of cleaning and sterilization required by conventional stainless steel mixing systems. This feature also ensures that sterility can be consistently maintained during repeated processing of multiple batches. In view of the foregoing, and the fact that the inventive systems are easily scalable, relatively low cost, and easily operated, the inventive systems can be used in a variety of industrial and research facilities that previously outsourced such processing.

Figure 1:
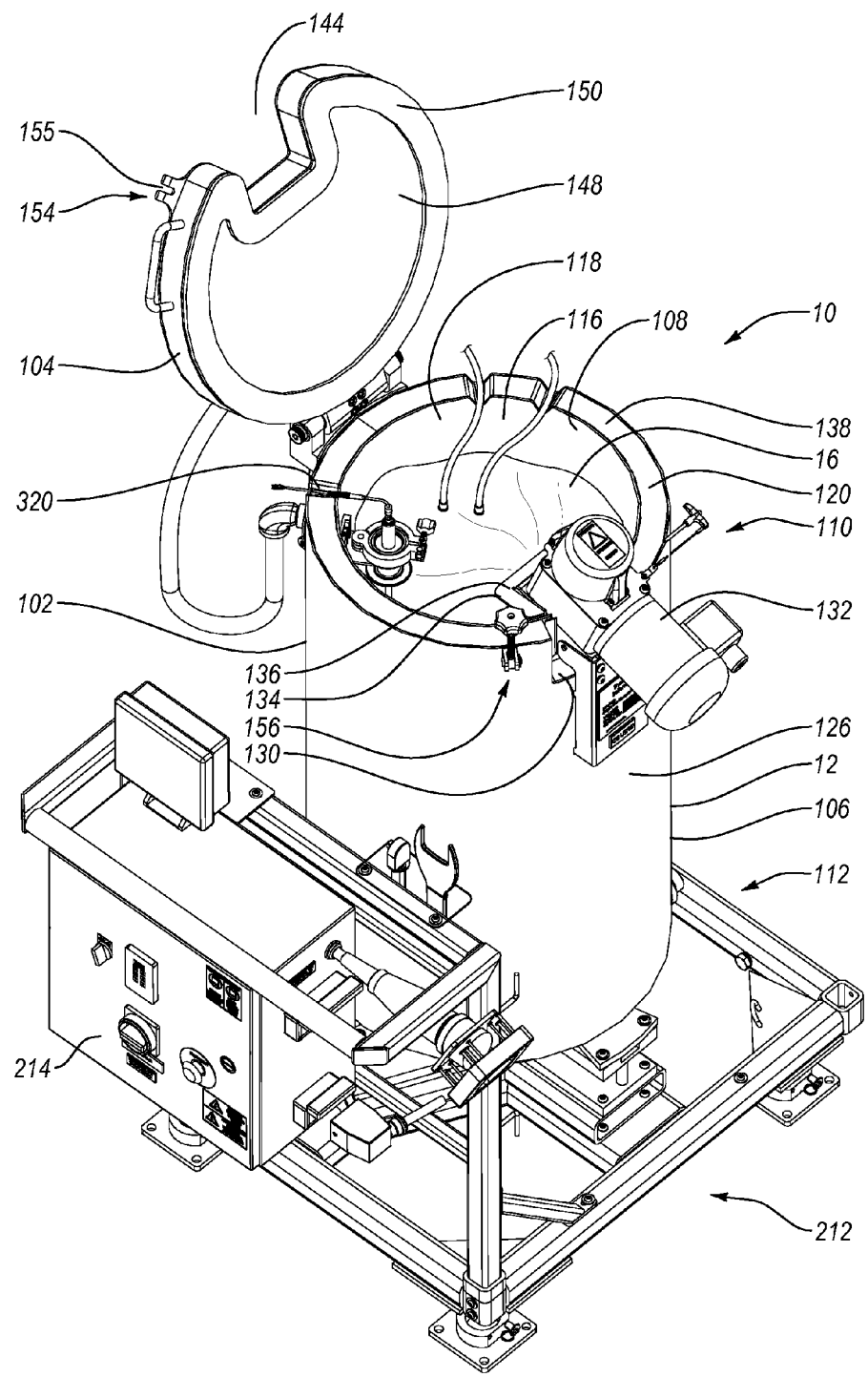
FIG. 1 is perspective view of a fluid heating system incorporating features of the present invention.

Depicted in FIG. 1 is one embodiment of an inventive fluid heating system 10 incorporating features of the present invention. In general, fluid heating system 10 comprises a tank assembly 12, a container assembly 16 that is disposed within and supported by tank assembly 12, and a drive shaft 18 (FIG. 2) that extends between tank assembly 12 and container assembly 16. Container assembly 16 houses the fluid or solution that is heated and can also be mixed and/or cooled. The various components of fluid heating system 10 will now be discussed in greater detail.

Figure 2:
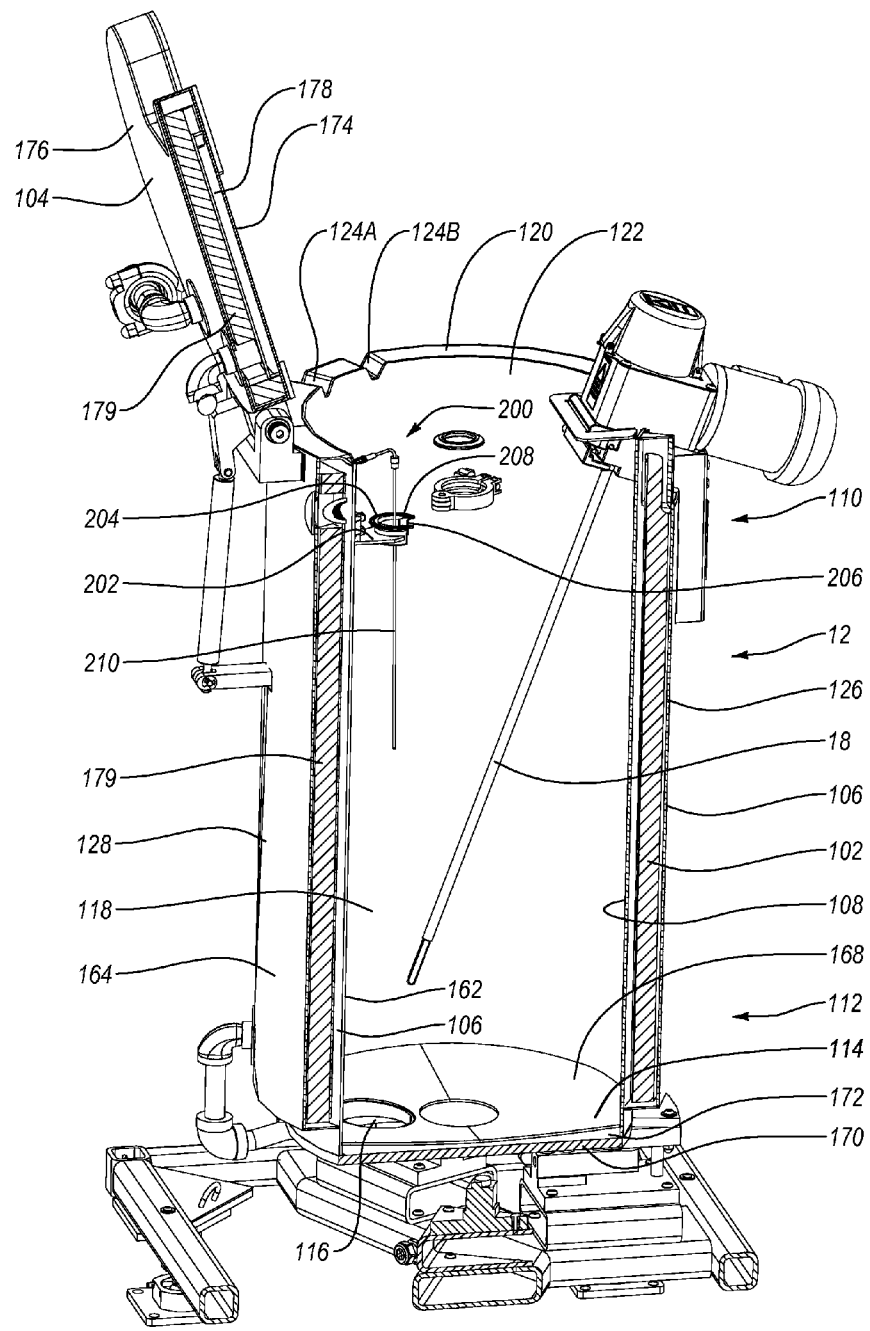
FIG. 2 is a cross sectional side view of the tank assembly of the fluid heating system shown in FIG. 1.

Continuing with FIG. 1, tank assembly 12 comprises a tank body 102 having a lid 104 hingedly coupled thereto. Tank body 102 comprises a substantially cylindrical sidewall 106 having an interior surface 108 that extends between an upper end 110 and an opposing lower end 112. As depicted in FIG. 2, tank body 102 also includes a floor 114 located at lower end 112 with a drain opening 116 extending therethrough. Interior surface 108 of sidewall 106 and floor 114 bound a chamber 118. As discussed below, chamber 118 is configured to receive container assembly 16 so that container assembly 16 is supported therein. A substantially C-shaped lip 120 is formed at upper end 110 of sidewall 106 and partially bounds an access opening 122 to chamber 118. A pair of spaced apart slots 124A and B are recessed on lip 120 and, as will be discussed below in greater detail, provide channels through which fluid lines can pass out of chamber 118 when lid 104 is closed.

In general, tank body 102 has a front face 126 and an opposing back face 128. As best shown in FIG. 1, an enlarged notch 130 is formed on front face 126 at upper end 110 and extends through sidewall 106 and lip 120. Disposed within notch 130 so as to communicate with chamber 118 is a drive motor assembly 132. As will be discussed below in greater detail, drive motor assembly 132 is used to rotate drive shaft 18 (FIG. 2) which in turn mixes the fluid within container assembly 16. Although not required, drive motor assembly 132 is typically fitted so that notch 130 is sealed closed. A generally U-shaped flange 134 having a top surface 136 extends between opposing sides of notch 130 along an inside face of drive motor assembly 132. Top surface 136 at opposing ends of flange 134 is flush with lip 120 so that lip 120 and flange 134 combine to form sealing surface 137 that bounds access opening 122 of chamber 118.

Figure 3:
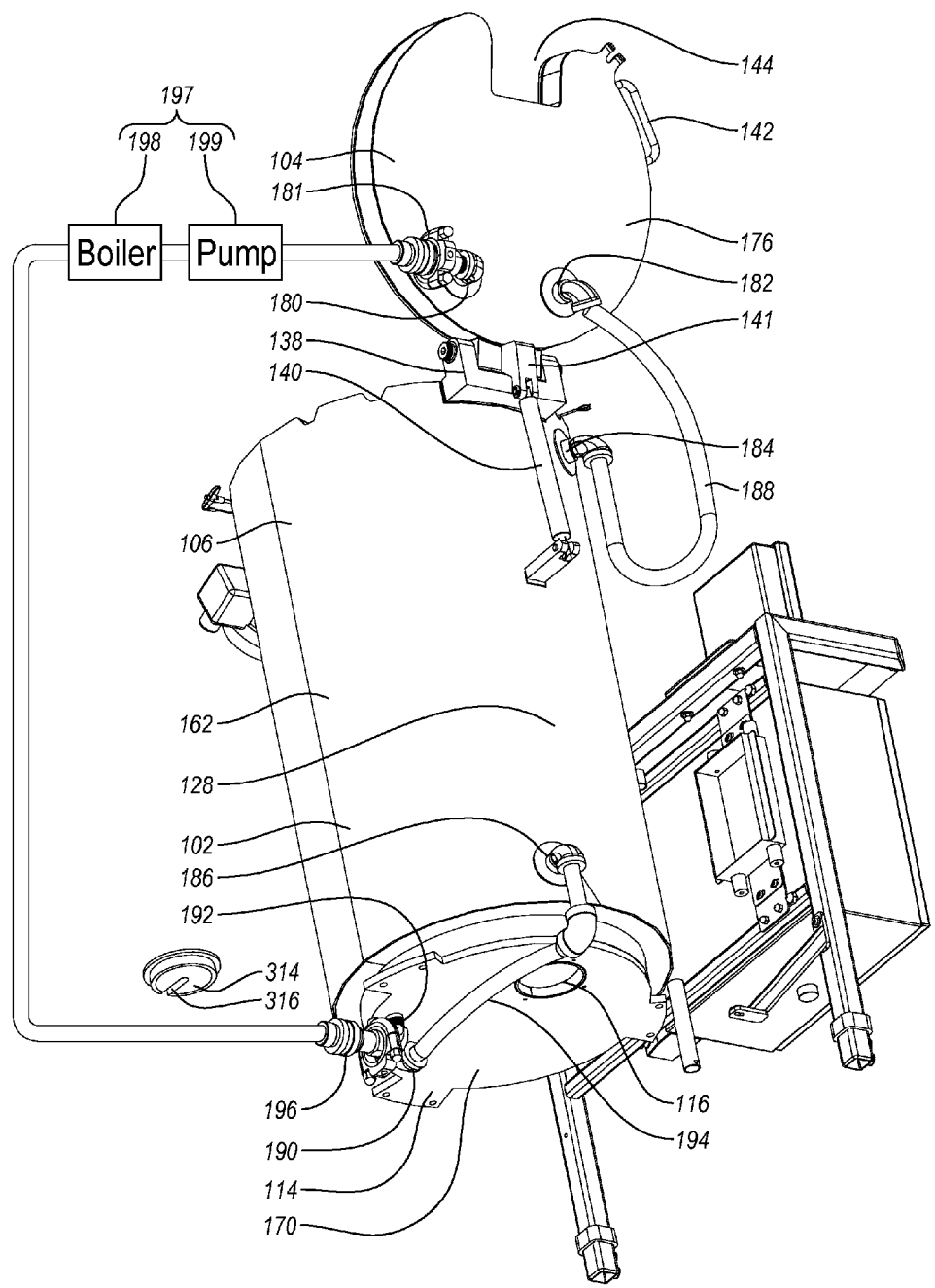
FIG. 3 is a bottom perspective view of the tank assembly shown in FIG. 2.
Figure 4:
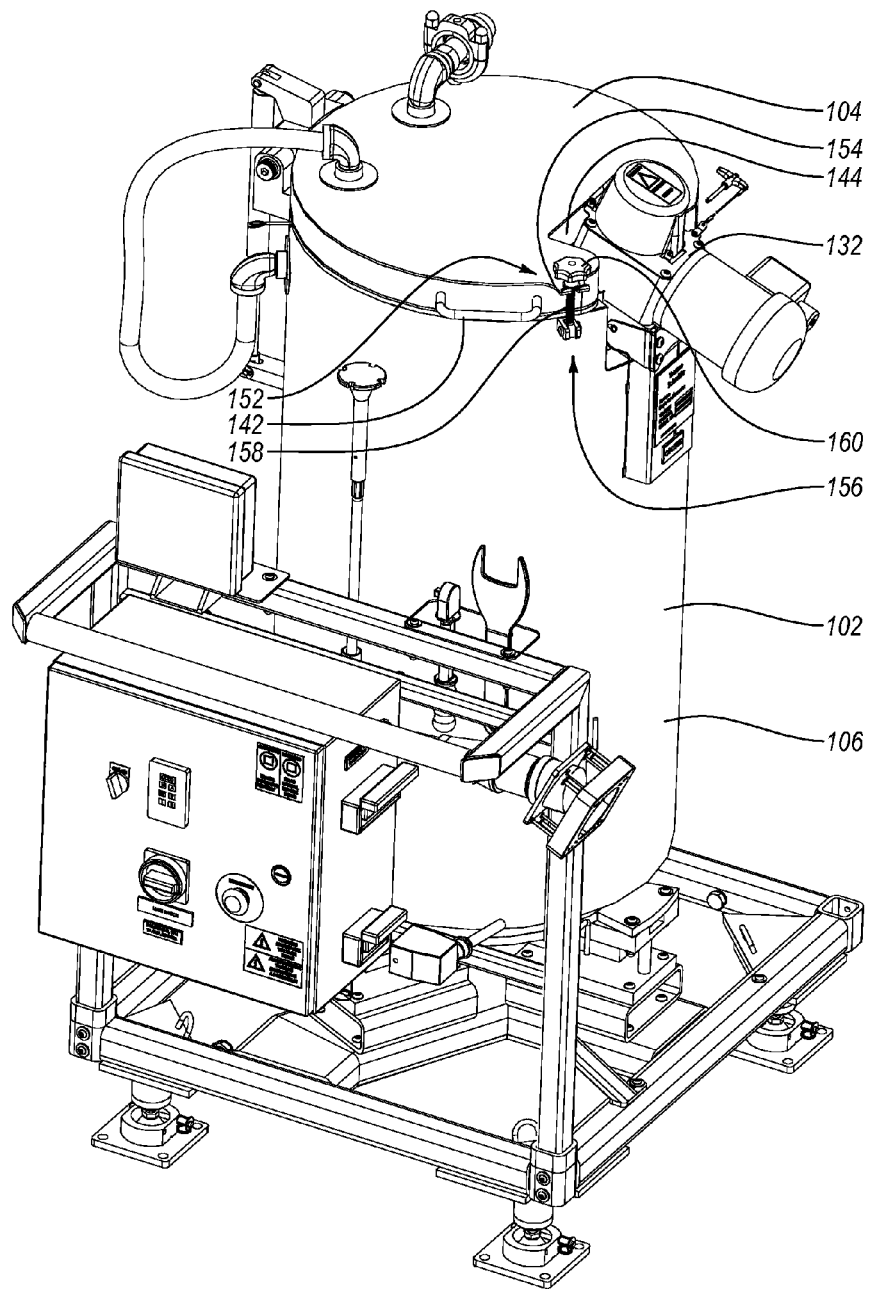
FIG. 4 is a perspective view of the tank assembly shown in FIG. 1 with the lid in a closed position.

As shown in FIG. 3, formed on back face 128 of tank body 102 is a hinge 138 that connects lid 104 to tank body 102. Hinge 138 enables lid 104 to be manually moved between an open position as shown in FIG. 1 and a closed position as shown in FIG. 4. A handle 142, shown in this embodiment as having a U-shaped configuration, is formed on lid 104 to assist in movement of lid 104 between the two positions. Continuing with FIG. 3, a piston 140 has a first end hingedly coupled with a lid portion 141 of hinge 138 and an opposing second end hingedly coupled with tank body 102. Piston 140 assists in smooth and controlled movement of lid 104 so that lid 104 does not unintentionally slam shut. Lid 104 has a notch 144 formed on a front face thereof opposite hinge 138. Notch 144 is sized to receive drive motor assembly 132 when lid 104 is in the closed position (FIG. 4). Returning to FIG. 1, lid 104 has an inside face 148 having a gasket 150 extending along a perimeter edge thereof. When lid 104 is in the closed position, gasket 150 sites on top of sealing surface 138 so that drain opening 116 to chamber 118 is substantially sealed closed. It is noted that when lid 104 is closed, slots 124A and B (FIG. 2) will still be open to chamber 118 which can be a source of heat loss. Such heat loss, however, is negligible. If desired, inserts can be placed within slots 124A and B to seal them off when not in use. In some embodiments, slots 124A and B can be eliminated.

As shown in FIG. 4, tank assembly 12 also includes a locking assembly 152 that helps to ensure a tight and secure sealed engagement between lid 104 and tank body 102. In the embodiment depicted, locking assembly 152 includes a catch 154 formed on and radially outwardly projecting out from lid 104. Catch 154 has a slot 155 (FIG. 1) formed on an end face thereof. In turn, a fastener 156 is mounted on tank body 102 below catch 154. Fastener 156 includes a threaded bolt 158 having a first end hingedly mounted to tank body 102 and an opposing second end having a handle 160 threaded thereon. When lid 104 is in the closed position, fastener 156 is rotated so that bolt 158 is received within slot 155 of catch 154. Handle 160 can then be selectively rotated to advance along bolt 158. In so doing, handle 160 biases against catch 154 and clamps lid 104 to tank body 102. If desired, two or more locking assemblies 152 can be used. In alternative embodiments, it is appreciated that the depicted locking assembly 152 can be replaced with any number of conventional locking systems such as latches, clamps, fasteners, screws, elastic cords, or any other structure that can temporarily secure lid 104 to tank body 102. In yet other embodiments, locking assembly 152 can be eliminated.

Although tank body 102 is shown as having a substantially cylindrical configuration, in alternative embodiments tank body 102 can have any desired shape capable of at least partially bounding a chamber. For example, sidewall 106 need not be cylindrical but can have a variety of other transverse, cross sectional configurations such as polygonal, elliptical, or irregular. Furthermore, it is appreciated that tank body 102 can be scaled to any desired size. For example, it is envisioned that chamber 118 of tank body 102 can be sized to hold a maximum volume of fluid in a range between about 50 liters to about 2,500 liters with about 75 liters to about 1,000 liters being common and about 75 liters to about 300 liters being more common. Other sizes can also be used. Tank body 102 and lid 104 are typically made of metal, such as stainless steel, but can also be made of other materials capable of withstanding the applied loads and temperatures of the present invention.

In one embodiment of the present invention means are provided for controlling the temperature of the fluid that is contained within container assembly 16 when container assembly 16 is disposed within chamber 118 of tank assembly 12. By way of example and not by limitation, tank body 102 and lid 104 can both be jacketed so as to bound one or more fluid channels through which heated or cooled fluid can pass. In turn, heat from the heated fluid flowing through tank assembly 12 radiates to the fluid within container assembly 16 for heating the fluid therein. Alternatively, chilled fluid flowing through tank assembly 12 draws heat from the fluid within container assembly 16 for cooling the fluid therein. For example, as shown in FIG. 2, sidewall 106 comprises an inside wall 162 and an outside wall 164 that bound a fluid channel 166 therebetween; floor 114 comprises an inside wall 168 and an outside wall 170 that bound a fluid channel 172 therebetween; and lid 104 comprises an inside wall 174 and an outside wall 176 that bound a fluid channel 178 therebetween. If desired an insulation layer 179 can be positioned between each outside wall 164, 170, and 176 and the corresponding fluid channel.

Turning to FIG. 3, outside wall 176 of lid 104 has an inlet port 180 and an outlet port 182 formed thereon and communicating with fluid channel 178 (FIG. 2). A hose coupling 181 is coupled with inlet port 180. Hose coupling 181 is designed to couple with a fluid line that extends from a thermal control unit (TCU) 197 or some other source for generating or providing a heated or cooled fluid so that the fluid can be pumped into fluid channel 178 at a desired temperature and flow rate. The fluid can be water, propylene glycol, or other types of fluids commonly used in this type of heating or cooling. In one embodiment, the TCU 197 can comprise a boiler 198 fluid coupled with a pump 199 which delivers the fluid to house coupling 181. A chiller and other components can also be used.

Outside wall 162 of sidewall 106 has an inlet port 184 and an outlet port 186 formed thereon and communicating with fluid channel 166 (FIG. 2). A fluid line 188 extends from outlet port 182 on lid 104 to inlet port 184 of sidewall 106 so that after the heated fluid passes through fluid channel 178 in lid 104 it can then pass through fluid channel 166 in sidewall 162. In turn, outside wall 170 of floor 114 has an inlet port 190 and an outlet port 192 formed thereon and communicating with fluid channel 172 (FIG. 2). A fluid line 194 extends from outlet port 186 on sidewall 106 to inlet port 190 of floor 114 so that after the heated fluid passes through fluid channel 166 in sidewall 162 it can then pass through fluid channel 172 in floor 114.

Finally, a hose coupling 196 is coupled with outlet port 192 of floor 114 so that a fluid line can be coupled therewith and extend back to TCU 197 where the fluid is then heated or cooled back to the desired temperature before repeating the cycle. The fluid flow system can thus be a close loop, recirculating system. It is appreciated that partitions or other structures can be formed within fluid channels 166, 172, and 178 to optimize fluid flow throughout so that tank body 102 and lid 104 apply a substantially uniform and continuous heat or cooling around all sides of container assembly 16 when container assembly 16 is disposed within tank assembly 12.

In alternative embodiments, it is appreciated that the heated or cooled fluid can enter through hose coupling 190 on floor 114 and then exit out through hose coupling 181 on lid 104. In still other embodiments, separate recirculating systems can be coupled with each of lid 104, sidewall 106 and/or floor 114. In contrast to using a heated liquid fluid, heated gas or steam can be used. Alternatively, the means for controlling the temperature can comprise electrical heating elements placed on the exterior surfaces of inside walls 162, 168, and 174. Other conventional heating or cooling systems can also be used. The means for controlling the temperature can be used to heat the fluid within container assembly 16 to a temperature in a range between about 30° C. to about 130° C. with about 50° C. to about 70° C. being more common. Other temperatures can also be used.

As also shown in FIG. 2, tank assembly 12 also includes a support 200 secured to interior surface 108 of sidewall 106 at upper end 110. Support 200 includes a flange 202 attached to and projecting from sidewall 106 and a substantially C-shaped retainer 204 disposed at the end thereof. Retainer 204 includes a stem 206 and a flange 208 radially outwardly projecting therefrom, both stem 206 and a flange 208 having a substantially C-shaped configuration. As will be discussed below in greater detail, support 200 is used for supporting a portion of container assembly 16 and for supporting a temperature probe 210 therein.

As shown in FIG. 1, tank assembly 12 is typically mounted on a platform 212. If desired, one or more load cells can be incorporated into platform 212 so that the quantity of fluid delivered to container assembly 12 when disposed within tank assembly 12 can be accurately measured. FIG. 1 also shows an electrical controller 214. Controller 214 can be used for measuring and controlling operational parameters such as the heat and flow rate of fluid through the fluid channels, as discussed above, tracking the time and temperature that the fluid within container assembly 12 is heated, measuring the weight of fluid entering container assembly 12 and controlling mixing of the fluid within container assembly 12 as will be discussed below in greater detail.

Figure 5:
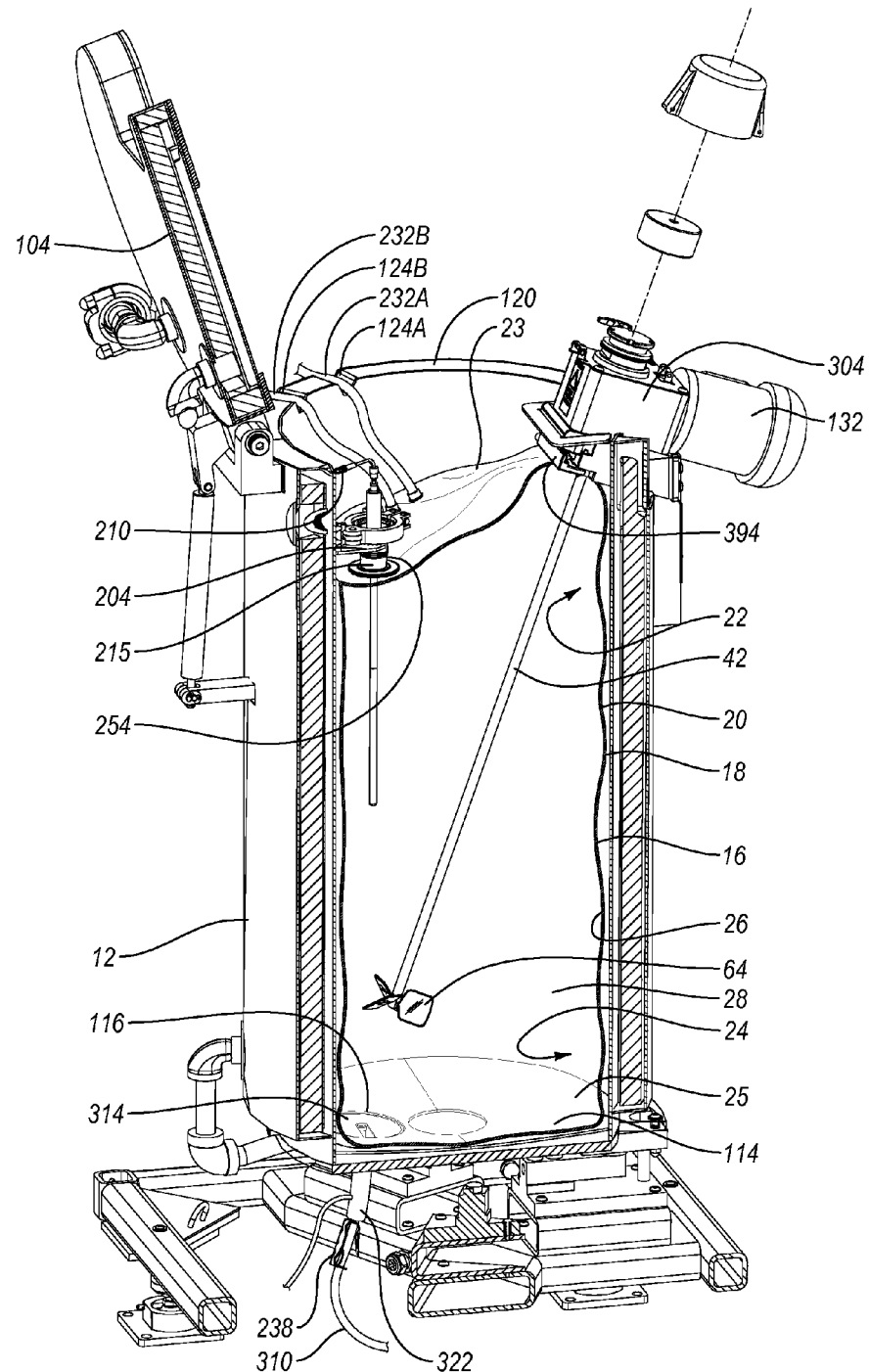
FIG. 5 is a cross sectional side view of the fluid heating system shown in FIG. 1.

Turning to FIG. 5, container assembly 16 comprises a container 18 having a side 20 that extends from an upper end 22 to an opposing lower end 24. Upper end 22 terminates at a top 23 while lower end 24 terminates at a bottom 25. Container 18 also has an interior surface 26 that bounds a compartment 28. Compartment 28 is configured to hold a fluid. In the embodiment depicted, container 18 comprises a flexible bag that is comprised of a flexible, water impermeable material such as a low-density polyethylene or other polymeric sheets having a thickness in a range between about 0.1 mm to about 5 mm with about 0.2 mm to about 2 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive.

The extruded material comprises a single integral sheet that comprises two or more layers of different materials that can be separated by a contact layer. All of the layers are simultaneously co-extruded. One example of an extruded material that can be used in the present invention is the HyQ CX3-9 film available from HyClone Laboratories, Inc. out of Logan, Utah. The HyQ CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the HyQ CX5-14 cast film also available from HyClone Laboratories, Inc. The HyQ CX5-14 cast film comprises a polyester elastomer outer layer, an ultra-low density polyethylene contact layer, and an EVOH barrier layer disposed therebetween. In still another example, a multi-web film produced from three independent webs of blown film can be used. The two inner webs are each a 4 mil monolayer polyethylene film (which is referred to by HyClone as the HyQ BM1 film) while the outer barrier web is a 5.5 mil thick 6-layer coextrusion film (which is referred to by HyClone as the HyQ BX6 film).

The material is approved for direct contact with living cells and is capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003 which are hereby incorporated by specific reference.

In one embodiment, container 18 comprise a two-dimensional pillow style bag wherein two sheets of material are placed in overlapping relation and the two sheets are bonded together at their peripheries to form the internal compartment. Alternatively, a single sheet of material can be folded over and seamed around the periphery to form the internal compartment. In another embodiment, container 18 can be formed from a continuous tubular extrusion of polymeric material that is cut to length and is seamed closed at the ends.

In still other embodiments, container 18 can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel is substantially identical and comprises a portion of the side wall, top end wall, and bottom end wall of the container. Corresponding perimeter edges of each panel are seamed. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1 that was published Sep. 19, 2002 of which the drawings and Detailed Description are hereby incorporated by reference.

Although in the above discussed embodiment container 18 has a flexible, bag-like configuration, in alternative embodiments it is appreciated that container 18 can comprise any form of collapsible container or semi-rigid container. Container 18 can also be transparent or opaque and can have ultraviolet light inhibitors incorporated therein.

It is appreciated that container 18 can be manufactured to have virtually any desired size, shape, and configuration. For example, container 18 can be formed having a compartment sized to 10 liters, 30 liters, 100 liters, 250 liters, 500 liters, 750 liters, 1,000 liters, 1,500 liters, 3,000 liters, 5,000 liters, 10,000 liters or other desired volumes and thus can be in a range between any of the above volumes. Although container 18 can be any shape, in one embodiment container 18 is specifically configured to be complementary or substantially complementary to chamber 118 of tank body 102, as discussed above.

In any embodiment, however, it is typically desirable that when container 18 is received within the chamber 118, container 18 is at least generally uniformly supported by tank body 102. Having at least general uniform support of container 18 by tank body 102 helps to preclude failure of container 18 by hydraulic forces applied to container 18 when filled with fluid.

Depicted in FIG. 6 is a front side view of container assembly 16 with container 18 in a folded or collapsed position. As shown therein, container assembly 16 includes ports 230A and B secured to upper end 22 of container 18. Ports 230A and B can be secured by welding or other conventional techniques and include a passageway extending therethrough that communicates with compartment 28 (FIG. 5). Coupled with and extending from ports 230A and B are fluid lines 232A and B, respectfully. Fluid lines 232A and B are typically comprised of a flexible hose or tubing. Mounted on the end of fluid line 232A and B are connectors 234A and B, respectfully. Connectors 234A and B are designed for forming a fluid coupling with an additional fluid line, container, or other structure. In one embodiment, connectors 234A and B can comprise aseptic connectors such as the KLEENPAK sterile connector available from the Pall Corporation. Other sterile or non-sterile connectors can also be used. An envelope 235 is removable positioned over each connector 234A and B to help maintain sterility prior to use. A tube clamp 238 can also be mounted on each fluid line 232A and B for closing the fluid lines or controlling the flow of gas or liquid therethrough. Fluid lines 232A and B are commonly used for delivering liquids, gases or other components into or out of container 18.

Also mounted at upper end 22 of container 18 is a port 240 having a gas line 242, typically in the form of a flexible hose or tube, extending therefrom and having a gas filter 244 mounted on the end thereof. Gas filter 244 typically has a barbed port 246 formed on the end thereof for removably receiving a gas line that is coupled with a compressor or other gas source. As will be discussed below in more detail, for proper positioning, expansion and filling of container 18, it is helpful to initially partially fill container 18 with a gas, such as air. The gas can be delivered through port 246 on gas filter 244. Gas filter 244 filters the gas so that no contaminates enter container 18. Once container assembly 16 is properly positioned within tank assembly 12, fluid and other components can be delivered into container 18 through one of fluid lines 232A or B while the displaced gas exits out through the other fluid line 232A or B. A tube clamp 238 can also be positioned on gas line 242 to selectively close off the passage therethrough.

Figure 8:
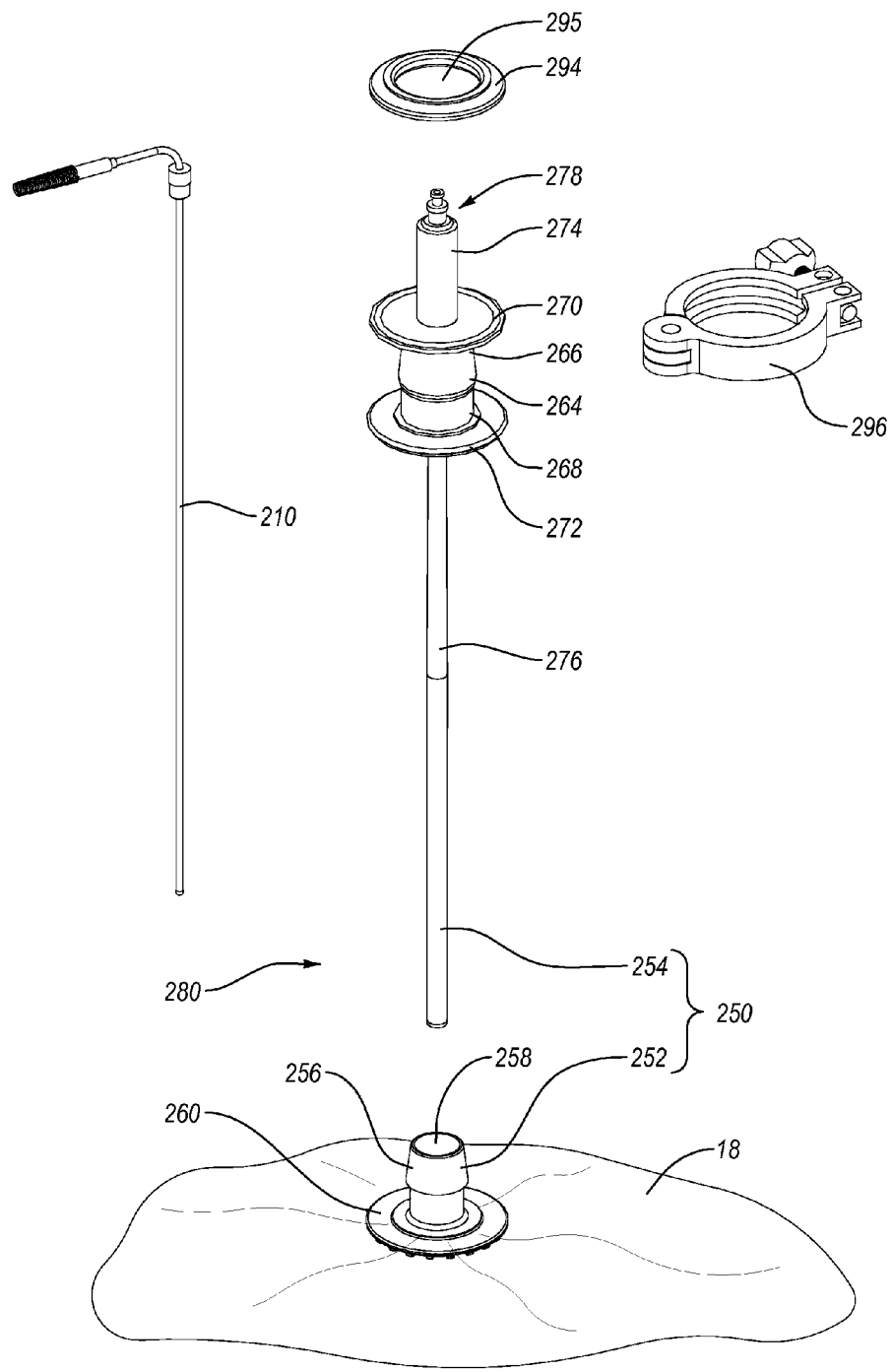
FIG. 8 is an exploded perspective view of a temperature port assembly of the container assembly shown in FIG. 6 with related parts.

Finally, also mounted at upper end 22 of container 18 is a temperature port assembly 250. Turning to FIG. 8, temperature port assembly 250 comprises a port 252 that is secured to container 18 and a probe adapter 254 that is coupled with port 252. Port 252 has a conventional design that includes a barbed stem 256 having a passage 258 extending therethrough and a flange 260 radially outwardly projecting therefrom. Flange 260 is welded or otherwise secured to container 18 so that passage 258 communicates with compartment 28 (FIG. 5). Probe adapter 254 comprises a flexible sleeve 264 having a first end 266 and an opposing second end 268. Encircling and radially outwardly projecting from first end 266 is a mounting flange 270. Likewise, encircling and radially outwardly projecting from second end 268 is a support flange 272. A tubular stem 274 projects in axial alignment with sleeve 264 from a side of mounting flange 270 opposite of sleeve 264.

Figure 9:
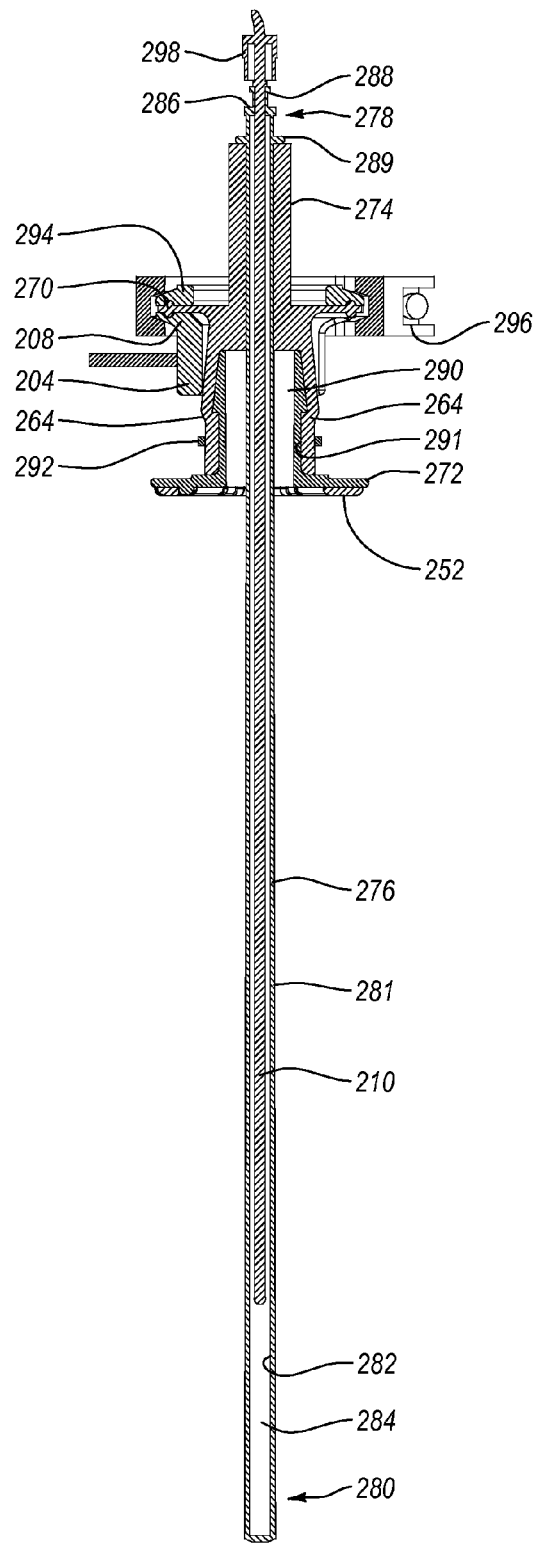
FIG. 9 is a cross sectional side view of the temperature port assembly shown in FIG. 8.

Probe adapter 254 also includes an elongated receiver 276 having a first end 278 and an opposing second end 280. As shown in FIG. 9, receiver 276 includes an elongated body 281 that typically has a substantially cylindrical configuration and extends between first end 278 and second end 280. Body 281 has an interior surface 282 that bound a cavity 284. Body 281 is closed except for an opening 286 formed at first end 278. A tubular catch 288 is mounted on and projects from first end 278 of body 281 in alignment with opening 286. A flange 289 encircles and radially outwardly projects from body 281 at first end 286.

During assembly, second end 280 of body 281 is passed down through stem 274, mounting flange 270, sleeve 264, and supporting flange 272 so that second end 280 projects down below support flange 272. Body is advanced until flange 289 rests against stem 274. In this configuration, a friction tight fit is formed between body 281 and stem 274. However, during radiation sterilization of container assembly 16, body 281 and stem 274 can weld together. Otherwise, if desired, an adhesive or other conventional welding techniques can be used to secure the structures together. In yet other embodiments, probe adapter 254 can be formed as a single unitary member or as other combinations of members secured together.

As also shown in FIG. 9, a cavity 290 is also formed between an interior surface 291 of sleeve 264 and the exterior surface of receiver 276. During assembly, port 252 is slid into cavity 290, the parts being sized so that a friction fit is formed therebetween. A tie 292 can then be cinched around sleeve 264 so as to ensure a liquid type seal between sleeve 264 and port 252.

In the assembled configuration, sleeve 264 is inserted within retainer 204 (FIG. 2) of tank body 102 so that mounting flange 270 rests on flange 208 of retainer 204. An annular gasket 294 having an opening 295 (FIG. 8) extending therethrough, is then positioned on top of mounting flange 270. Finally, a clamp 296 (FIG. 8), such as a tri-clamp, is positioned around flange 208, mounted flange 270 and gasket 294 so that when clamp 296 is closed and tightened, these structures are securely held together. Port 252 and the portion of container 18 secured thereto are thus secured to and supported by retainer 204. An elongated temperature probe 210, commonly referred to as an RTD, can be advanced down into cavity 284 of receiver 276. A collar 298 mounted on probe 210 can be threaded onto catch 288 so as to secure temperature probe 210 to receiver 276.

By inserting temperature probe 210 within receiver 276, temperature probe 210 can measure the temperature of the fluid within container 18 through the wall of receiver 276. Receiver 276 protects temperature probe 210 from directly contacting the fluid within container 18. As such, there is no risk of temperature probe 210 contaminating the fluid and temperature probe 210 can be reused without sterilization or other cleaning. Furthermore, temperature probe 210 is rigidly held in position at a distance spaced apart from sidewall 162. As such, temperatures probe 210 give a more accurate reading of the temperature of the fluid than if it was positioned adjacent to sidewall 162. Temperatures probe 210 is also held at a constant location independent of whether fluid is being added or removed from container 18.

Returning to FIG. 6, container assembly 16 also comprises a port 308 mounted at lower 24 of container 18, a drain line 310 extending from port 308, and a tube connector 312, such as a sterile connector, mounted at the end of drain line 310. A hose clamp 238 is also mounted on drain line 310 for closing the passage therethrough. Finally, a support plate 314 is shown encircling drain line 310 adjacent to port 308. As shown in FIG. 3, drain opening 116 is typically formed oversized so that it is easy to reach up through drain opening 116 and grab drain line 310 or to otherwise pass drain line 310 down through drain opening 116. Support plate 314 is simply a plate that is configured to be received within drain opening 116 after drain line 310 passes therethrough so that container 18 can be supported thereon. Support plate 314 can have a slot 316 extending therethrough and radially extending in from the perimeter edge so that drain line 310 can be removably slid into slot 316. Alternatively, support plate 314 can simply have a central hole through which drain line 310 is passed during the assembly of container assembly 16.

If desired, other ports can be mounted on container 18 for use in coupling other probes to container 18. For example, other ports can be used for coupling probes such as pH probes, dissolved oxygen probes, and the like. Examples of ports and how various probes and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference. Ports can also be used for coupling container 18 to secondary containers, to condenser systems, and to other desired fittings.

Figure 10:
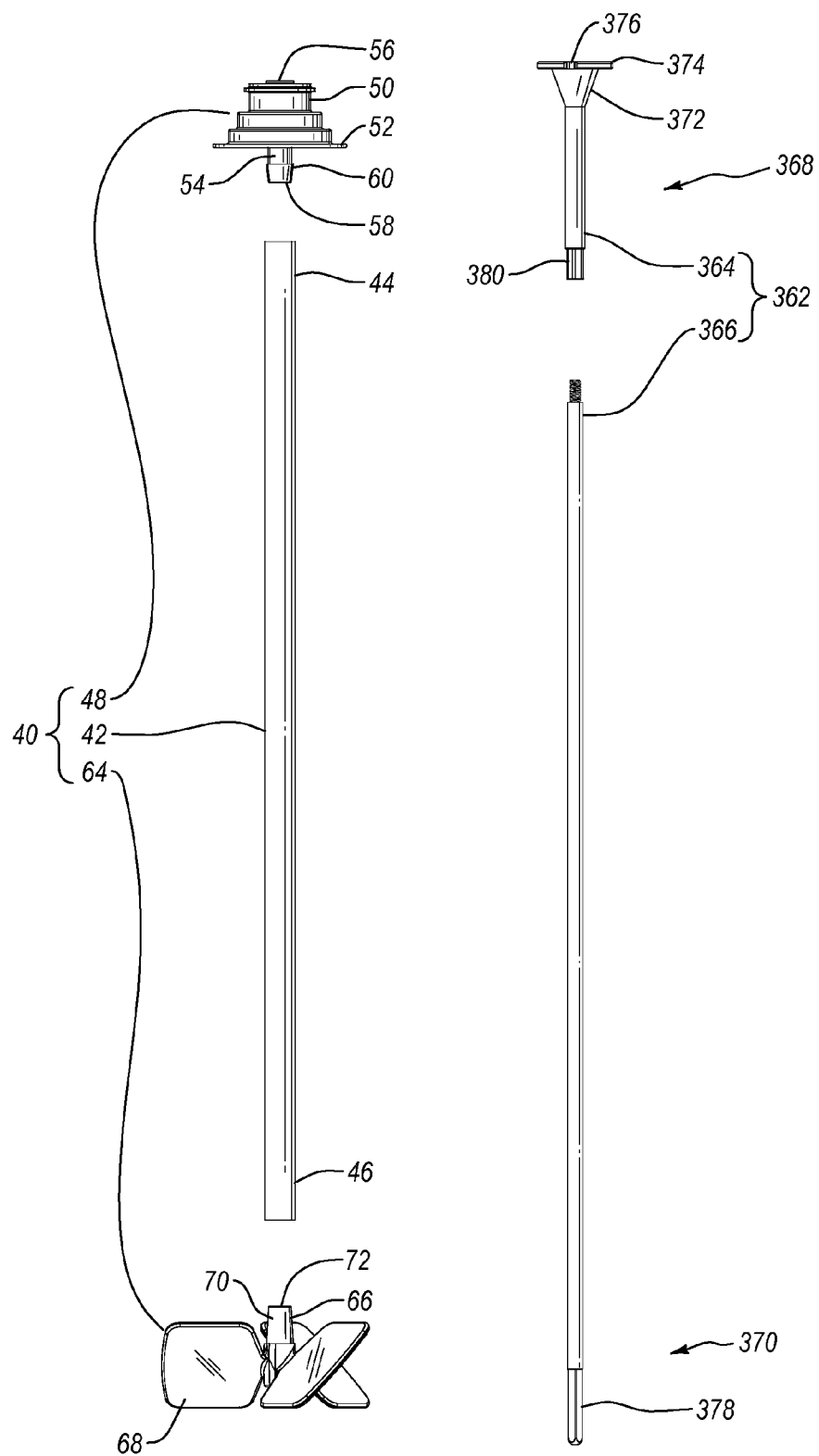
FIG. 10 is an elevated side view of an impeller assembly and drive shaft used in the fluid heating system.

Depicted in FIG. 7 is a back side view of container assembly 16 with container 18 in a folded or collapsed position. As shown therein, container assembly 16 further comprises an impeller assembly 40. As depicted in FIG. 10, impeller assembly 40 comprises an elongated tubular connector 44 having a rotational assembly 48 mounted at one end and an impeller 64 mounted on the opposing end. More specifically, tubular connector 44 has a first end 46 and an opposing second end 48 with a passage 50 that extends therebetween. In one embodiment, tubular connector 44 comprises a flexible tube such as a polymeric tube. In other embodiments, tubular connector 44 can comprise a rigid tube or other tubular structures.

Rotational assembly 48 is mounted to first end 46 of tubular connector 44. Rotational assembly 48 comprises an outer casing 50 having an outwardly projecting flange 52 and a tubular hub 54 rotatably disposed within outer casing 50. A bearing assembly can be disposed between outer casing 50 and tubular hub 54 to permit free and easy rotation of hub 54 relative to casing 50. Likewise, one or more seals can be formed between outer casing 50 and tubular hub 54 so that during use an aseptic seal can be maintained between outer casing 50 and tubular hub 54 as tubular hub 54 rotates relative to outer casing 50.

Hub 54 has an interior surface 56 that bounds an opening 58 extending therethrough. As will be discussed below in greater detail, an engaging portion of interior surface 56 has a polygonal or other non-circular transverse cross section so that a driver portion of drive shaft 362 passing through opening 58 can engage the engaging portion and facilitate rotation of hub 54 by rotation of drive shaft 362. Hub 54 can also comprise a tubular stem 60 projecting away from outer casing 50. Hub 54 can couple with first end 44 of tubular connector 42 by stem 60 being received within first end 44. A pull tie, clamp, crimp or other fastener can then be used to further secure stem 60 to tubular connect 42 so that a liquid tight seal is formed therebetween. Other conventional connecting techniques can also be used.

Impeller 64 comprises a central hub 66 having a plurality of fins 68 radially outwardly projecting therefrom. It is appreciated that a variety of different numbers and configurations of fins 68 can be mounted on hub 66. Hub 66 has a first end 70 with a blind socket 72 formed thereat. Socket 72 typically has a non-circular transverse cross section, such as polygonal, so that it can engage a driver portion of drive shaft 362. Accordingly, as will be discussed below in greater detail, when a driver portion is received within socket 72, the driver portion engages with impeller 64 such that rotation of drive shaft 362 facilities rotation of impeller 64.

In one embodiment, hub 66 and fins 68 of impeller 64 are molded from a polymeric material. In alternative embodiments, hub and fins 68 can be made of metal, composite, or a variety of other materials. If desired, an annular insert can be positioned within socket 72 to help reinforce hub 66. For example, the insert can be comprised of metal or other material having a strength property greater than the material from which hub 66 is comprised.

Impeller 64 can be attached to connector 42 by inserting first end 70 of hub 66 within connector 42 at second end 46. A pull tie, clamp, crimp, or other type of fastener can then be cinched around second end 46 of connector 42 so as to form a liquid tight sealed engagement between impeller 64 and connector 42.

Returning to FIG. 7, rotational assembly 48 is secured to container 18 so that tubular connector 42 and impeller 64 extend into or are disposed within compartment 28 of container 18 (FIG. 5). Specifically, in the depicted embodiment container 18 has an opening 74 at upper end 22. Flange 52 of outer casing 50 is sealed around the perimeter edge bounding opening 74 so that hub 54 is aligned with opening 74. Tubular connector 42 having impeller 64 mounted on the end thereof projects from hub 54 into compartment 28 of container 18. In this configuration, outer casing 50 is fixed to container 18 but hub 54, and thus also tubular connector 42 and impeller 64, can freely rotate relative to outer casing 50 and container 18. As a result of rotational assembly 48 sealing opening 74, compartment 28 is sealed closed so that it can be used in processing sterile fluids.

As depicted in FIG. 10, impeller assembly 40 is used in conjunction with drive shaft 362. In general drive shaft 362 comprises a head section 364 and a shaft section 366 that can be coupled together by threaded connection or other techniques. Alternatively, draft shaft 362 can be formed as a single piece member or from a plurality of attachable sections. Drive shaft 362 has a first end 368 and an opposing second end 370. Formed at first end 368 is a frustoconical engaging portion 372 that terminates at a circular plate 374. Notches 376 are formed on the perimeter edge of circular plate 374 and are used for engaging drive shaft 362 with drive motor assembly 132 as will be discussed below.

Formed at second end 370 of drive shaft 362 is a driver portion 378. Driver portion 378 has a non-circular transverse cross section so that it can facilitate locking engagement within hub 66 of impeller 64. In the embodiment depicted, driver portion 378 has a polygonal transverse cross section. However, other non-circular shapes can also be used. A driver portion 380 is also formed along drive shaft 362 toward first end 368. Driver portion 380 also has a non-circular transverse cross section and is positioned so that it can facilitate locking engagement within the interior surface of hub 54 of rotational assembly 48.

During use, as will be discussed below in further detail, drive shaft 362 is advanced down through hub 54 of rotational assembly 48, through tubular connector 42 and into hub 66 of impeller 64. As a result of the interlocking engagement of driver portions 378 and 380 with hubs 66 and 54, respectively, rotation of drive shaft 362 by a drive motor assembly facilitates rotation of hub 54, tubular connector 42 and impeller 64 relative to outer casing 50 of rotational assembly 48. As a result of the rotation of impeller 64, fluid within container 18 is mixed.

It is appreciated that impeller assembly 40, drive shaft 362 and the discrete components thereof can have a variety of different configuration and can be made of a variety of different materials. Alternative embodiments of and further disclosure with respect to impeller assembly 40, drive shaft 362, and the components thereof are disclosed in US Publication Number 2011/0188928, published Aug. 4, 2011 which is incorporated herein in its entirety by specific reference.

Figure 11:
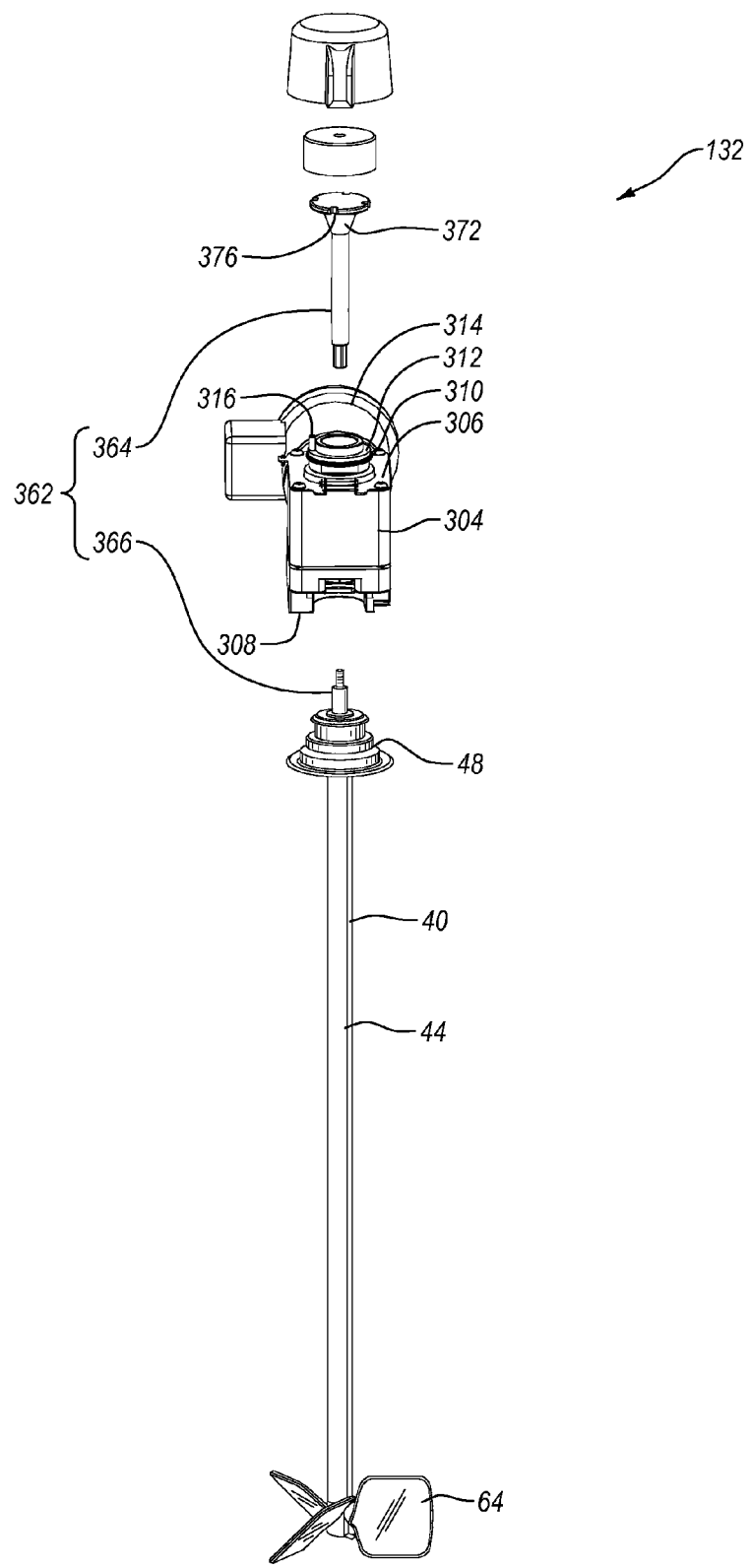
FIG. 11 is a partially disassembled perspective view of the impeller assembly, drive shaft and drive motor assembly of the fluid heating system.

As previously discussed with regard to FIG. 1, tank assembly 12 comprises drive motor assembly 132 mounted to sidewall 106. Drive motor assembly 132 is used in conjunction with drive shaft 362 (FIG. 10) and can be used for mixing and/or suspending a culture, solution, or other fluids within container 18 (FIG. 2). Turning to FIG. 11, drive motor assembly 132 comprises a housing 304 having a top surface 306 and an opposing bottom surface 308. An opening 310 extends through housing 304 from top surface 306 to bottom surface 308. A tubular motor mount 312 is rotatably secured within opening 310 of housing 304. Upstanding from motor mount 312 is a locking pin 316. A drive motor 314 is mounted to housing 304 and engages with motor mount 312 so as to facilitate select rotation of motor mount 312 relative to housing 304. Drive shaft 362 is configured to pass through motor mount 312 so that engaging portion 372 of drive shaft 362 is retained within motor mount 312 and locking pin 316 of motor mount 312 is received within notch 376 of drive shaft 362. As a result, rotation of motor mount 312 by drive motor 314 facilitates rotation of drive shaft 362. Further discussion of drive motor assembly 132 and how it engages with drive shaft 362 and alternative designs of drive motor assembly 132 are provided in US Publication Number 2011/0188928 which was previously incorporated herein by specific reference.

Figure 12:
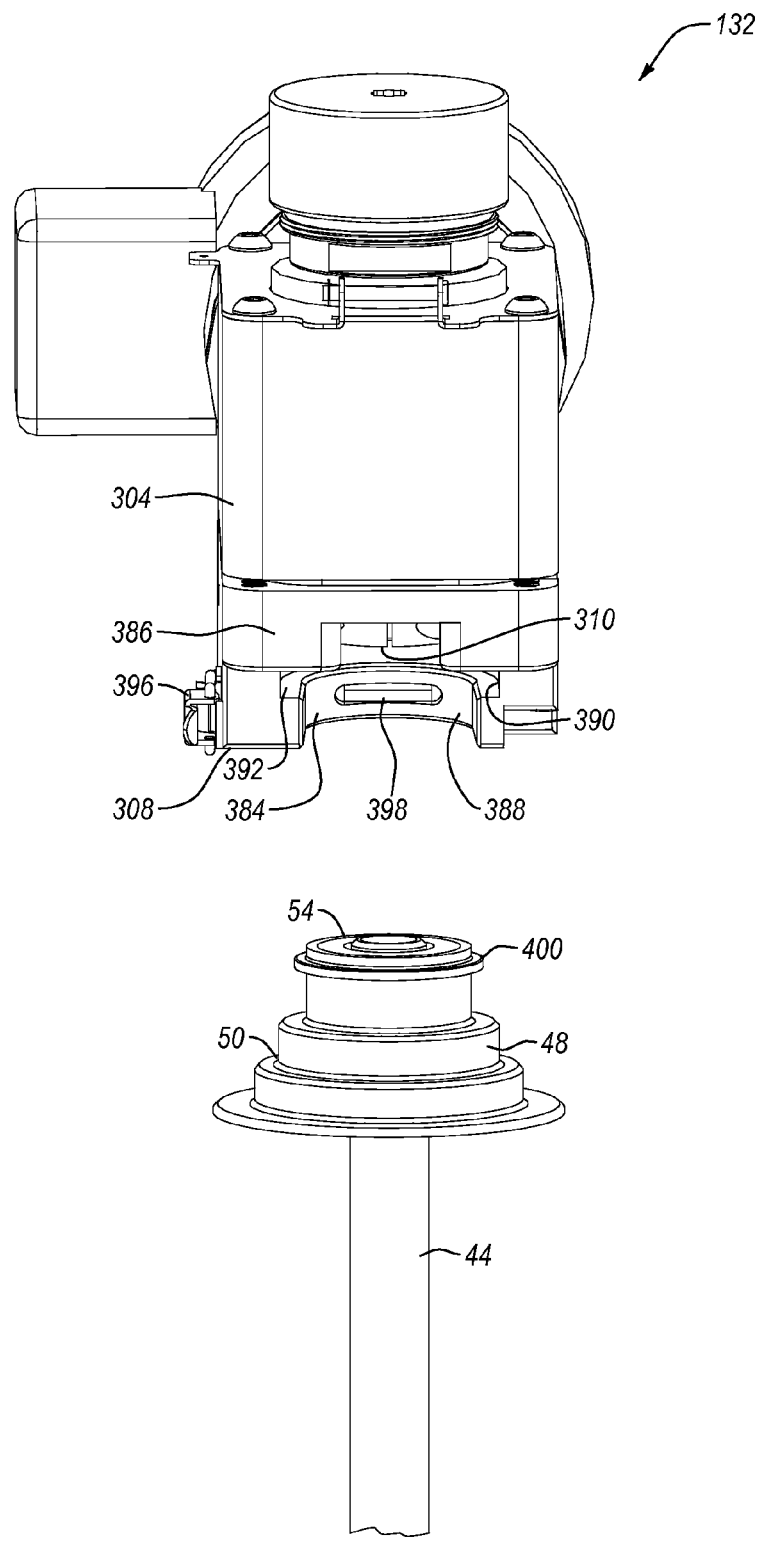
FIG. 12 is an enlarged view of the rotational assembly and drive motor assembly in a disassembled view state.

To facilitate operation, rotational assembly 48 is coupled with drive motor assembly 132. Specifically, as depicted in FIG. 12, housing 304 of drive motor assembly 132 has an open access 384 that is recessed on a front face 386 so as to communicate with opening 310 extending through housing 304. Access 384 is in part bounded by a substantially C-shaped first side wall 388 that extends up from bottom surface 308, a concentrically disposed substantially C-shaped second side wall 390 disposed above first side wall 388 and having a diameter larger than first side wall 388, and a substantially C-shaped shoulder 392 extending between side walls 388 and 390. As shown in FIG. 5, a door 394 is hingedly mounted to housing 304 and selectively closes the opening to access 384 from front face 386. Returning to FIG. 12, door 394 is secured in a closed position by a latch 396. Positioned on first side wall 388 is a section 398 of a resilient and/or elastomeric material such as silicone. Other sections 398 of similar materials can also be positioned on first side wall 388 or the interior surface of door 394.

Figure 13:
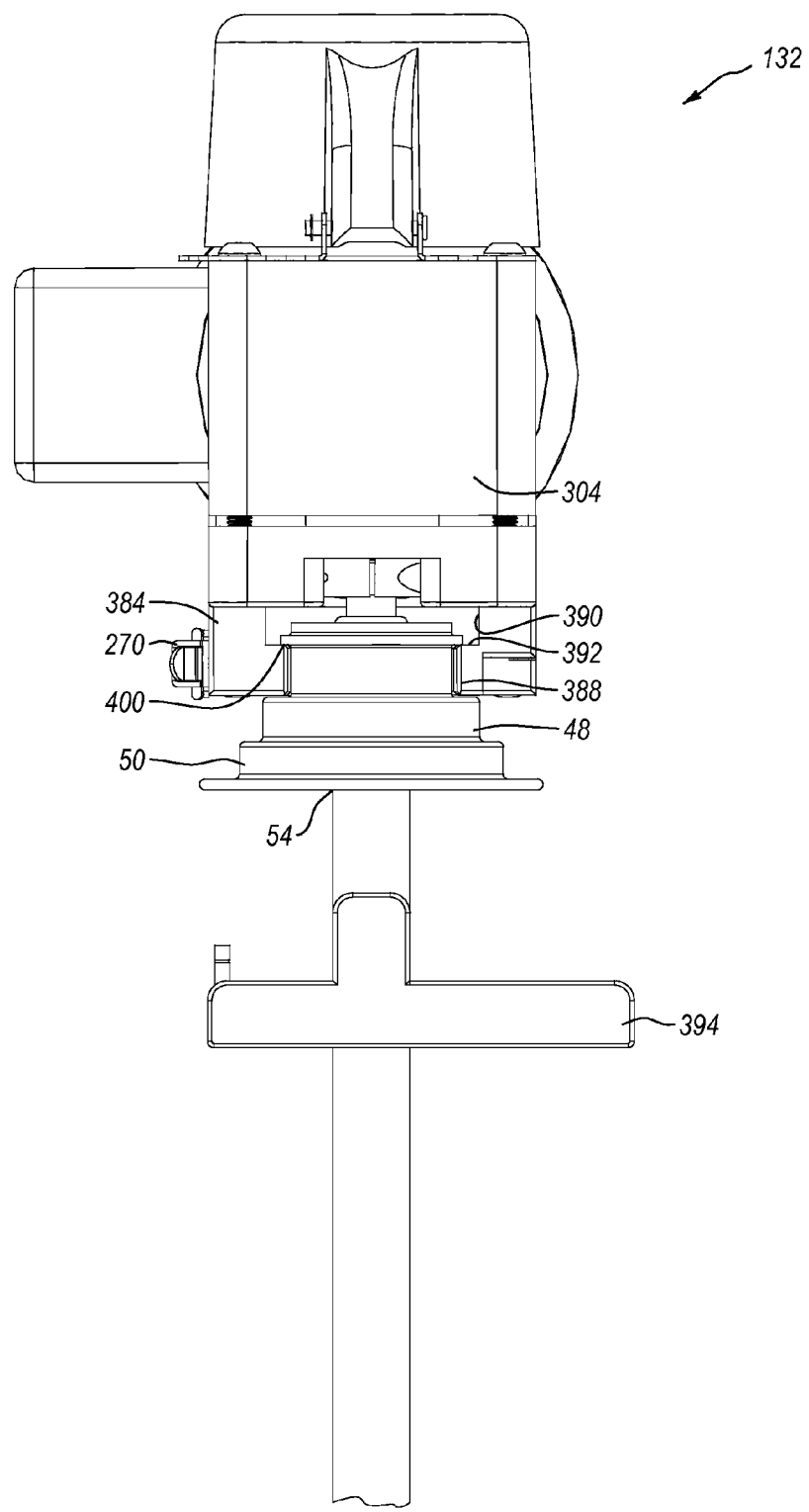
FIG. 13 is an elevated front view of the rotational assembly and drive motor assembly coupled together.

As depicted in FIG. 13, to facilitate attachment of rotational assembly 48 to housing 304, with door 394 rotated to an open position, rotational assembly 48 is horizontally slid into access 384 from front face 386 of housing 304 so that a support flange 400 radially outwardly extending from an upper end of rotational assembly 48 rests on shoulder 392 of access 384. Rotational assembly 48 is advanced into access 384 so that the passage extending through hub 54 of rotational assembly 48 aligns with the passage extending through motor mount 312 (FIG. 11). In this position, door 394 (FIG. 5) is moved to the closed position and secured in the closed position by latch 396. As door 394 is closed, casing 50 of rotational assembly 48 is biased against the one or more sections 398 (FIG. 12) of resilient material so as to clamp rotational assembly 48 within access 384 and thereby prevent unwanted rotational movement of casing 50 relative to housing 304 of drive motor assembly 132.

Once rotational assembly 48 is secured to drive motor assembly 132, drive shaft 362 (FIG. 10) can be advanced down through drive motor assembly 132 and into impeller assembly 40 so as to engage impeller 64. Once drive shaft 362 is properly positioned, drive motor assembly 132 can activated causing drive shaft 362 to rotate impeller 64 and thereby mix or suspend the fluid within container 18.

On embodiment of the present invention includes means for mixing the fluid within container 18. One example of such means comprises impeller assembly 40, draft shaft 362 and drive motor assembly 132. In alternative embodiments of the means for mixing, impeller assembly 40 can be replaced with a drive shaft that extends through a dynamic seal on container 18 and has an impeller mounted on the end thereof within container 18. In yet other embodiments, the means for mixing can comprise a stir bar, impeller or other form of mixer disposed within container 18 and a magnetic mixer disposed outside of container 18 that can rotate the mixer within container 18 through the use of a magnetic force. Other conventional mixers can also be used.

One typical example of how the inventive fluid heating system 10 can be used will now be provided. Initially, container assembly 16 is fabricated at a plant so that it is collapsed and sterilized as a complete assembly. Either just prior to or after placement of container assembly 16 within compartment 28 of tank assembly 12, container assembly 16 is partially filled with a gas through gas filter 244 (FIG. 6). By so doing, container assembly 16 expands enabling it to be easily positioned within and coupled to tank assembly 12. Specifically, as shown in FIG. 5, drain line 310 is passed out through drain opening 116 in floor 114 and support plate 314 is fitted within drain opening 116; temperature port assembly 215 is coupled with retainer 204 of tank assembly 12 and rotational assembly 48 of container assembly 16 is coupled with drive motor assembly 132 of tank assembly 12 each has previously discussed. At different stages, more gas can be injected into container assembly 16 to ensure proper placement and coupling of container assembly 16 and to avoid any potential risk of kinking container 18 as it is filled with liquid.

Once container assembly 16 is properly positioned, fluid line 232A is coupled with a fluid source while fluid line 232B is coupled with a gas outlet line. These couplings are made aseptically so as to ensure no breach and sterility. The desired fluid is then dispensed into container 18 through fluid line 232A while the displace gas is passed out through fluid line 232B. As desired, the fluid and components thereof can be delivered in different stages. For example, container assembly 16 can initially be substantially filled with media followed by delivering a culture of cells or microorganisms. During this fluid filling and gas evacuation process, fluid lines 232A and 232B can pass out of tank assembly 12 through slots 124A and B on lip 120. This ensures that if lid 104 is closed, that the fluid lines are not damaged. At some stage, temperature probe 210 is secured within probe adaptor 254 as discussed above. The electrical wires extending from temperature probe 210 can likewise pass out through a slot 320 formed on lip 120 of tank assembly 12 as shown in FIG. 1, so as to avoid any damage thereto when lid 104 is closed.

With rotational assembly 48 secured to drive motor assembly 132, drive shaft 362 is passed down through drive motor assembly 132 and into impeller assembly 40 where it couples with impeller 64. Once all of the attachments and couplings are complete and container 18 is filled with the desired fluid, clamps 238 are closed on fluid lines 232A and 232B (FIG. 6) so as to close off any further communications through the lines. Fluid lines 232A and 232B can then be disconnected from the fluid source and the gas outlet line after which the entire fluid lines 232A and 232B can be coiled and placed on top of container 18 within tank assembly 12. Lid 104 is then closed and locked in place using fastener 156.

Either before or after closing lid 104, drive motor assembly 132 is activated to begin mixing fluid within container assembly 16. This mixing of the fluid is not always required by helps to ensure that all of the fluid is uniformly heated within container 18. Furthermore, the mixing helps to ensure that the fluid is homogeneous when it is dispensed for subsequent use. Heated fluid is pumped through the jacket of tank assembly 12 so that fluid within container 18 is heated. The heating can be started at any stage, i.e., before or after disconnecting fluid line 232A from the fluid source. By having lid 104 closed and all sides of tank assembly 12 heated, along with the fluid in container 18 being mixed, the fluid can be uniformly and accurately heated with precision. The fluid is typically heated to a desired temperature after which that temperature is maintained for desired period of time to achieve desired results.

For example, to inactivate yeast, the fluid within container 18 is heated to a temperature of approximately 60° and maintained at that temperature for approximately 75 minutes. The temperature and the time for maintaining the temperature can vary depending on the desired processing. Furthermore, the temperature may be raised or lowered at different stages. Likewise, in contrast to using tank assembly 12 for heating, it is also appreciated that chilled fluid can be passed through the jacket of tank assembly 12 for chilling the fluid within container assembly 16.

To ensure that all of the fluid in container assembly 16 is properly heated, an electrical heating element 322, as shown in FIG. 5, can be wrapped around the portion of drain line 310 extending between contain 18 and clamp 238. Electrical heating element 322 can heat the fluid within drain line 310 to the same temperature as the fluid within container 18. This ensure proper heating of the fluid within drain line 310. Clamp 238 is not opened until after all of the fluid has been properly heated.

Once the fluid within container assembly 16 has been properly processed, the heating can be discontinued. Drain line 310 can then be coupled in a sterile manner with a container or further line for draining fluid from container 18. If desired, mixing of the fluid within container 18 may continue to ensure that the fluid is homogeneous as it is dispensed.

When the processing is complete, drive shaft 362 is removed and rotational assembly 48 is separated from drive motor assembly 132. Container assembly 16 can then be separated from tank assembly 12 and disposed of. A second container assembly 16 can then be couple with tank assembly 12 in the same manner as discussed above and the process repeated.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for inactivating a fluid culture, the method comprising:
   inserting a collapsible bag within a chamber of a tank assembly;
   dispensing a fluid into a compartment of the collapsible bag, the fluid comprising a culture containing live cells or microorganisms;
   positioning a lid over an opening of the tank assembly so that the collapsible bag is substantially enclosed within the tank assembly;
   heating the fluid within the collapsible bag to an inactivation temperature that is sufficiently high to kill all of the live cells or microorganisms within the fluid; and
   mixing the fluid within the flexible bag while the fluid is being heated to the inactivation temperature.

2. The method as recited in claim 1, further comprising an elongated fluid line having a first end fluid coupled with the collapsible bag and an opposing second end that is freely disposed, the method further comprising inserting the freely disposed second end of the fluid line into the chamber of tank assembly so that the second end is substantially enclosed within the chamber during heating of the fluid within the collapsible bag.

3. The method as recited in claim 1, wherein the step of heating the fluid comprises pumping a heated fluid through a sidewall and the lid of the tank assembly.

4. The method as recited in claim 1, wherein the step of mixing comprises rotating a mixing element within the collapsible bag.

5. The method as recited in claim 1, wherein the step of mixing comprises:
   advancing a drive shaft through a drive motor assembly, through a hub rotatably mounted on the collapsible bag, and into an elongated tubular connector coupled with the hub, an impeller being coupled with the tubular connector; and
   activating the drive motor assembly so that the drive motor assembly rotates the drive shaft which in turn rotates the impeller within the compartment of the collapsible bag.

6. The method as recited in claim 1, wherein the collapsible bag is inserted into the chamber of the tank assembly through the opening over which the lid is subsequently positioned.

7. The method as recited in claim 1, wherein the tank assembly comprises a sidewall encircling the chamber and the lid is hingedly mounted to the sidewall.

8. The method as recited in claim 1, further comprising:
   a temperature port assembly coupled to the collapsible bag, the temperature port assembly bounding a cavity that projects into the compartment of the collapsible bag but is not in fluid communication with the compartment; and
   a temperature probe positioned with the cavity of the temperature port assembly.

9. The method as recited in claim 8, further comprising securing the temperature port assembly to a support inwardly projecting from an interior surface of a sidewall of the tank assembly so that the support supports the temperature port assembly within the chamber of the tank assembly at a distance from the sidewall.

10. A method for inactivating a fluid culture, the method comprising:
    inserting a collapsible bag within a chamber of a tank assembly, the collapsible bag having a temperature port assembly coupled thereto, the temperature port assembly bounding a cavity that projects into a compartment of the collapsible bag but is not in fluid communication with the compartment;

securing the temperature port assembly to a support projecting from an interior surface of a sidewall of the tank assembly so that the support supports the temperature port assembly within the chamber of the tank assembly at a distance from the sidewall;

inserting a temperature probe with the cavity of the temperature port assembly;

dispensing a fluid into a compartment of the collapsible bag, the fluid comprising a culture containing live cells or microorganisms; and heating the fluid within the collapsible bag to an inactivation temperature that is sufficiently high to kill all of the live cells or microorganisms within the fluid.

11. The method as recited in claim 10, wherein the support comprises:
   a flange mounted to the sidewall of the tank assembly and projecting into the chamber; and
   a retainer disposed at an end of the flange, the temperature port assembly being supported on the retainer.

12. The method as recited in claim 11, further comprising using a clamp to secure the temperature port assembly to the retainer.

13. The method as recited in claim 10, wherein the temperature port assembly comprises:

a port secured to the flexible bag; and
a probe adapter secured to the port, the probe adapter comprising:
   a tubular sleeve received over the port;
   a mounting flange radially outwardly projecting from the sleeve; and
   a receiver coupled to the sleeve and projecting down through the sleeve, the receiver bounding the cavity of the temperature port assembly.

14. The method as recited in claim 10, wherein the step of dispensing the fluid into the collapsible bag comprises delivering media into the collapsible bag and delivering the live cells or microorganisms into the collapsible bag either concurrently with the media or after delivery of the media.

15. The method as recited in claim 10, further comprising mixing the fluid within the flexible bag while the fluid is being heated to the inactivation temperature.

16. The method as recited in claim 10, further comprising:
   the collapsible bag being inserted into the chamber of the tank assembly through an opening on the tank assembly; and
   positioning a lid over the opening of the tank assembly while the fluid is being heated to the inactivation temperature.

* * * * *